United States Patent
Wu et al.

(10) Patent No.: US 11,332,431 B2
(45) Date of Patent: May 17, 2022

(54) DEVICE AND METHOD FOR MANUFACTURING DIMETHYL CARBONATE

(71) Applicant: National Tsing Hua University, Hsinchu (TW)

(72) Inventors: Tsai-Wei Wu, Taipei (TW); I-Lung Chien, Taipei (TW); San-Jang Wang, Hsinchu (TW); David S. H. Wong, Hsinchu (TW); En-Ko Lee, Hsinchu (TW); Shi-Shang Jang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 43 days.

(21) Appl. No.: 16/896,229

(22) Filed: Jun. 9, 2020

(65) Prior Publication Data

US 2021/0323905 A1 Oct. 21, 2021

(30) Foreign Application Priority Data

Apr. 16, 2020 (TW) ................ 109112736

(51) Int. Cl.
*C07C 68/04* (2006.01)
*B01D 3/14* (2006.01)
(Continued)

(52) U.S. Cl.
CPC .............. *C07C 68/04* (2013.01); *B01D 3/009* (2013.01); *B01D 3/06* (2013.01); *B01D 3/148* (2013.01); *B01J 4/002* (2013.01); *B01J 8/0278* (2013.01)

(58) Field of Classification Search
CPC .......... C07C 68/04; B01D 3/009; B01D 3/06; B01D 3/148; B01J 4/002; B01J 8/0278
See application file for complete search history.

(56) References Cited

U.S. PATENT DOCUMENTS 5,274,163 A 12/1993 Rechner et al.
5,359,118 A * 10/1994 Wagner ................ C07C 68/065
203/DIG. 6

(Continued)

FOREIGN PATENT DOCUMENTS

CN 1156720 8/1997
CN 1036336 11/1997

(Continued)

OTHER PUBLICATIONS

Office Action of Taiwan Counterpart Application, dated Feb. 2, 2021, pp. 1-3.

(Continued)

*Primary Examiner* — Jonathan Miller
(74) *Attorney, Agent, or Firm* — JCIPRNET

(57) ABSTRACT

A device for manufacturing dimethyl carbonate including a reaction section and a separation section is provided. The reaction section includes a first distillation column, a methanol supply device, a carbon dioxide supply device, a dehydrating agent supply device, and a side reactor. The methanol supply device is connected to the first distillation column. The carbon dioxide supply device is connected to the first distillation column. The dehydrating agent supply device is connected to the first distillation column. A feed nozzle of the side reactor is connected to a gas outlet of a top of the first distillation column. A discharge nozzle of the side reactor is connected to a recycle nozzle of the first distillation column. A catalyst is disposed in the side reactor. The separation section includes a second distillation column. The second distillation column is connected to a liquid outlet of a bottom of the first distillation column.

20 Claims, 2 Drawing Sheets

(51) Int. Cl.
  B01J 4/00        (2006.01)
  B01D 3/00        (2006.01)
  B01J 8/02        (2006.01)
  B01D 3/06        (2006.01)

(56) References Cited

U.S. PATENT DOCUMENTS

| | | | | |
|---|---|---|---|---|
| 5,543,548 | A * | 8/1996 | Landscheidt | C07C 68/00 |
| | | | | 558/277 |
| 7,074,951 | B2 * | 7/2006 | Ryu | C07C 68/00 |
| | | | | 558/262 |
| 7,279,592 | B2 * | 10/2007 | Ryu | C07C 68/00 |
| | | | | 558/262 |
| 7,314,947 | B2 * | 1/2008 | Ryu | C07C 68/00 |
| | | | | 558/262 |
| 9,656,942 | B2 * | 5/2017 | Ii | C07C 68/065 |
| 9,765,014 | B2 * | 9/2017 | Wang | C07C 68/065 |
| 9,796,656 | B1 * | 10/2017 | Panchal | C07C 68/08 |
| 10,941,105 | B1 * | 3/2021 | Panchal | B01D 5/006 |
| 2005/0203307 | A1 | 9/2005 | Ryu et al. | |

FOREIGN PATENT DOCUMENTS

| | | |
|---|---|---|
| CN | 1138736 | 2/2004 |
| CN | 1241900 | 2/2006 |
| CN | 101830806 | 7/2013 |
| CN | 103922888 | 7/2014 |
| CN | 105801408 | 7/2016 |
| CN | 104761429 | 8/2017 |
| CN | 108640838 | 10/2018 |

OTHER PUBLICATIONS

Tsai-Wei Wu, et al., "CO2 Utilization Feasibility Study: Dimethyl Carbonate Direct Synthesis Process with Dehydration Reactive Distillation," Industrial & Engineering Chemistry Research 2020, vol. 59, No. 3, Dec. 30, 2019, pp. 1234-1248.

Bor-Yih Yu, et al., "Assessment on CO2 Utilization through Rigorous Simulation: Converting CO2 to Dimethyl Carbonate," Industrial & Engineering Chemistry Research 2018, vol. 57, No. 2, Dec. 15, 2017, pp. 639-652.

Xutao Hu, et al., "Analysis of direct synthesis of dimethyl carbonate from methanol and CO2 intensified by in-situ hydration-assisted reactive distillation with side reactor," Chemical Engineering and Processing: Process Intensification, vol. 129, Jul. 2018, pp. 109-117.

Pichayapan Kongpanna, et al., "Techno-economic evaluation of different CO2-based processes for dimethyl carbonate production," Chemical Engineering Research and Design, vol. 93, Jan. 2015, pp. 496-510.

Masayoshi Honda, et al., "Catalytic CO2 conversion to organic carbonates with alcohols in combination with dehydration system," Catalysis Science & Technology, vol. 4, Issue 9, May 2014, pp. 2830-2845.

Jun Bian, et al., "Highly effective synthesis of dimethyl carbonate from methanol and carbon dioxide using a novel copper-nickel/graphite bimetallic nanocomposite catalyst," Chemical Engineering Journal, vol. 147, No. 2, Apr. 15, 2009, pp. 287-296.

Kai-Yi Hsu, et al., "Design and Control of Dimethyl Carbonate-Methanol Separation via Extractive Distillation in the Dimethyl Carbonate Reactive-Distillation Process," Industrial & Engineering Chemistry Research 2010, vol. 49, No. 2, Dec. 4, 2009, pp. 735-749.

J. De La Torre, et al., "Liquid-liquid equilibria of the system dimethyl carbonate + methanol + water at different temperatures," Fluid Phase Equilibria, vol. 247, Issues 1, Sep. 15, 2006, pp. 40-46.

Erdogan Alper, et al., "CO2 utilization: Developments in conversion processes," Petroleum, vol. 3, Issue 1, Mar. 2017, pp. 109-126.

William L. Luyben, "Estimating refrigeration costs at cryogenic temperatures," Computers and Chemical Engineering, vol. 103, Aug. 4, 2017, pp. 144-150.

Ming Xia, et al., "Two-Stripper/Flash/Distillation Column System Design, Operation, and Control for Separating 2-Pentanone/4-Heptanone/Water Azeotropic Mixture via Navigating Residue Curve Maps and Balancing Total Annual Cost and Product Loss," Industrial & Engineering Chemistry Research 2018, vol. 57, No. 2, Nov. 10, 2017, pp. 689-702.

Tiansheng Zhao, et al., "Novel reaction route for dimethyl carbonate synthesis from CO2 and methanol," Fuel Processing Technology, vol. 62, Issues 2, Feb. 2000, pp. 187-194.

Yoshiki Ikeda, et al., "Promoting effect of phosphoric acid on zirconia catalysts in selective synthesis of dimethyl carbonate from methanol and carbon dioxide," Catalysis Letters, vol. 66, No. 1, Jan. 2000, pp. 59-62.

Keiichi Tomishige, et al., "Catalytic and direct synthesis of dimethyl carbonate starting from carbon dioxide using CeO2—ZrO2 solid solution heterogeneous catalyst: effect of H2O removal from the reaction system," Applied Catalysis A: General, vol. 237, Issues 1, Nov. 2002, pp. 103-109.

X.L. Wu, et al., "Direct synthesis of dimethyl carbonate on H3PO4 modified V2O5," Journal of Molecular Catalysis A: Chemical, vol. 238, Issues 1, Sep. 1, 2005, pp. 158-162.

X.L. Wu, et al., "Direct synthesis of dimethyl carbonate (DMC) using Cu—Ni/VSO as catalyst," Journal of Molecular Catalysis A: Chemical, vol. 249, Issues 1, Apr. 18, 2006, pp. 93-97.

Yuichi Yoshida, et al., "Direct synthesis of organic carbonates from the reaction of CO2 with methanol and ethanol over CeO2 catalysts," Catalysis Today, vol. 115, Issues 1, Jun. 30, 2006, pp. 95-101.

X.J. Wang, et al., "Direct synthesis of dimethyl carbonate from carbon dioxide and methanol using supported copper (Ni, V, O) catalyst with photo-assistance," Journal of Molecular Catalysis A: Chemical, vol. 278, Issues 1, Dec. 14, 2007, pp. 92-96.

Kyung Won LA, et al., "Effect of acid-base properties of H3PW12O40/CexTi1-xO2 catalysts on the direct synthesis of dimethyl carbonate from methanol and carbon dioxide: A TPD study of H3PW12O40/CexTi1-xO2 catalysts," Journal of Molecular Catalysis A: Chemical, vol. 269, Issues 1, May 18, 2007, pp. 41-45.

Michele Aresta, et al., "Cerium(IV)oxide modification by inclusion of a hetero-atom: A strategy for producing efficient and robust nano-catalysts for methanol carboxylation," Catalysis Today, vol. 137, Issue 1,Aug. 30, 2008, pp. 125-131.

Danielle Ballivet-Tkatchenko, et al., "Carbon dioxide conversion to dimethyl carbonate: The effect of silica as support for SnO2 and ZrO2 catalysts," Comptes Rendus Chimie, vol. 14, Issues 7, Jul. 2011, pp. 780-785.

J. Bian, et al., "Direct synthesis of dimethyl carbonate over activated carbon supported Cu-based catalysts," Chemical Engineering Journal, vol. 165, Issue 2, Dec. 1, 2010, pp. 686-692.

Ahmed Aouissi, et al., "Gas-Phase Synthesis of Dimethyl Carbonate from Methanol and Carbon Dioxide Over Co1.5PW12O40 Keggin-Type Heteropolyanion," International Journal of Molecular Sciences, vol. 11, No. 4, Mar. 31, 2010, pp. 1343-1351.

Zhang, Zhifang, et al., "Direct Synthesis of DMC from CO2 and CH3OH over CexZr 1-x-0.1Y0.1O2 Catalysts," Advanced Materials Research, vol. 287-290, Jul. 2011, pp. 1632-1635.

Hye Jin Lee, et al., "Direct Synthesis of Dimethyl Carbonate from Methanol and Carbon Dioxide over Ga2O3/Ce0.6Zr0.4O2 Catalysts: Effect of Acidity and Basicity of the Catalysts," Catalysis Letters, vol. 141, No. 4, Mar. 2011, pp. 531-537.

Jun Bian, et al., "Graphene nanosheet as support of catalytically active metal particles in DMC synthesis," Chinese Chemical Letters, vol. 22, Issue 1, Jan. 2011, pp. 57-60.

Masayoshi Honda, et al., "Ceria-catalyzed conversion of carbon dioxide into dimethyl carbonate with 2-cyanopyrdine," ChemSusChem, Aug. 2013, vol. 6, No. 8, pp. 1341-1344.

B.A.V. Santos, et al., "Kinetic study for the direct synthesis of dimethyl carbonate from methanol and CO2 over CeO2 at high pressure conditions," Applied Catalysis A: General, vol. 455, Mar. 30, 2013, pp. 219-226.

Atul Bansode, et al., "Continuous DMC Synthesis from CO2 and Methanol over a CeO2 Catalyst in a Fixed Bed Reactor in the Presence of a Dehydrating Agent," ACS Catalysis, vol. 4, No. 11, Sep. 29, 2014, pp. 3877-3880.

(56) References Cited

OTHER PUBLICATIONS

Meng Zhang, et al., "Cerium oxide-based catalysts made by template-precipitation for the dimethyl carbonate synthesis from Carbon dioxide and methanol," Journal of Cleaner Production, vol. 103, Sep. 15, 2015, pp. 847-853.
Rim Saada, et al., "Greener synthesis of dimethyl carbonate using a novel ceria—zirconia oxide/graphene nanocomposite catalyst," Applied Catalysis B: Environmental, vols. 168-169, Jun. 2015, pp. 353-362.
Unnikrishnan P, et al., "Direct synthesis of dimethyl carbonate from CO2 and methanol over CeO2 catalysts of different morphologies," Journal of Chemical Sciences, vol. 128, No. 6, Jun. 2016, pp. 957-965.
Satish K. Kabra, et al., "Direct synthesis of dimethyl carbonate from methanol and carbon dioxide: A thermodynamic and experimental study," The Journal of Supercritical Fluids, vol. 117, Nov. 2016, pp. 98-107.
Sanny Verma, et al., "Fixation of carbon dioxide into dimethyl carbonate over titanium-based zeolitic thiophene-benzimidazolate framework," Scientific Reports, vol. 7, No. 655, Apr. 5, 2017, pp. 1-5.
Dragos Stoian, et al., "Improving the Stability of CeO2 Catalyst by Rare Earth Metal Promotion and Molecular Insights in the Dimethyl Carbonate Synthesis from CO2 and Methanol with 2-Cyanopyridine," ACS Catalysis, vol. 8, No. 4, Mar. 5, 2018, pp. 3181-3193.
Yanfeng Pu, et al., "Synthesis of dimethyl carbonate from CO2 and methanol over a hydrophobic Ce/SBA-15 catalyst," RSC Advances, vol. 8, No. 48, Jul. 2018, pp. 27216-27226.

\* cited by examiner

DEVICE AND METHOD FOR MANUFACTURING DIMETHYL CARBONATE

CROSS-REFERENCE TO RELATED APPLICATION

This application claims the priority benefit of Taiwan application serial no. 109112736, filed on Apr. 16, 2020. The entirety of the above-mentioned patent application is hereby incorporated by reference herein and made a part of this specification.

BACKGROUND

Technical Field

The disclosure relates to a device and a method for manufacturing a compound, in particular, to a device and a method for manufacturing dimethyl carbonate (DMC).

Description of Related Art

Performing a conversion reaction by utilizing carbon dioxide as a raw material so as to synthesize a more valuable chemical is a carbon reduction strategy much developed in recent years. Dimethyl carbonate (DMC) has wide applications and can be used as raw materials of other compounds (such as polycarbonate (PC)), a lithium battery solution or a fuel additive, etc., and therefore, it is also one of popular research directions to convert carbon dioxide into DMC.

Methods for manufacturing DMC by utilizing carbon dioxide include a direct synthesis method, a direct urea alcoholysis method, a transesterification method and an indirect urea alcoholysis method, and the simplest synthesis way therein is the direct synthesis method. The direct synthesis method directly synthesizes DMC and water through a catalyst reactor by taking carbon dioxide and methanol as reactants. The direct synthesis method is simple in reaction, and chemicals included by the whole system are less than those of other synthesis methods. However, how to improve a reaction conversion rate and reduce manufacturing procedure energy consumption, a total annual cost (TAC) as well as carbon emission is currently an objective for continuous research.

SUMMARY

The invention provides a device and a method for manufacturing dimethyl carbonate, which may effectively improve a reaction conversion rate and reduce manufacturing procedure energy consumption, a total annual cost as well as carbon emission.

The invention proposes a device for manufacturing dimethyl carbonate, including a reaction section and a separation section. The reaction section includes a first distillation column, a methanol supply device, a carbon dioxide supply device, a dehydrating agent supply device, and a side reactor. The methanol supply device is connected to the first distillation column. The carbon dioxide supply device is connected to the first distillation column. The dehydrating agent supply device is connected to the first distillation column. A feed nozzle of the side reactor is connected to a gas outlet of a top of the first distillation column. A discharge nozzle of the side reactor is connected to a recycle nozzle of the first distillation column. A catalyst is disposed in the side reactor. The separation section includes a second distillation column. The second distillation column is connected to a liquid outlet of a bottom of the first distillation column.

According to an embodiment of the invention, in the above device for manufacturing the dimethyl carbonate, the second distillation column may be an only distillation column in the separation section.

According to an embodiment of the invention, in the above device for manufacturing the dimethyl carbonate, the second distillation column may be only connected to the first distillation column, and is not connected to other distillation columns.

According to an embodiment of the invention, in the above device for manufacturing the dimethyl carbonate, the recycle nozzle of the first distillation column may be located between the top and the bottom of the first distillation column.

According to an embodiment of the invention, in the above device for manufacturing the dimethyl carbonate, the methanol supply device may be connected to a methanol feed nozzle of the first distillation column. The carbon dioxide supply device may be connected to a carbon dioxide feed nozzle of the first distillation column. The dehydrating agent supply device may be connected to a dehydrating agent feed nozzle of the first distillation column.

According to an embodiment of the invention, in the above device for manufacturing the dimethyl carbonate, the methanol feed nozzle may be higher than the carbon dioxide feed nozzle. The carbon dioxide feed nozzle may be higher than the dehydrating agent feed nozzle.

According to an embodiment of the invention, in the above device for manufacturing the dimethyl carbonate, the recycle nozzle may be as high as the dehydrating agent feed nozzle.

According to an embodiment of the invention, in the above device for manufacturing the dimethyl carbonate, a splitter is further included. The splitter is connected between the gas outlet of the top of the first distillation column and the feed nozzle of the side reactor. The splitter may include a first splitting nozzle and a second splitting nozzle. The first splitting nozzle of the splitter is connected to the feed nozzle of the side reactor.

According to an embodiment of the invention, in the above device for manufacturing the dimethyl carbonate, a condenser and a flash vessel may further be included. The condenser is connected to the second splitting nozzle of the splitter. The flash vessel is connected to the condenser.

According to an embodiment of the invention, in the above device for manufacturing the dimethyl carbonate, a first backflow pipeline and a second backflow pipeline may further be included. The first backflow pipeline is connected between a gas outlet of the flash vessel and the first distillation column. The second backflow pipeline is connected between a liquid outlet of the flash vessel and the first distillation column.

The invention proposes a method for manufacturing dimethyl carbonate, including the following steps: making a reactant including methanol and carbon dioxide enter a first distillation column; making the reactant in the first distillation column enter a side reactor; conducting a main reaction in the side reactor including a catalyst, so as to form a first product including the dimethyl carbonate and water; making a discharge material flow of the side reactor flow back to the first distillation column, wherein the discharge material flow of the side reactor includes the first product; conducting a dehydrating reaction in the first distillation column by using a dehydrating agent so as to make the dehydrating agent fully react with the water in the first distillation column to form a second product; making a discharge material flow of a bottom of the first distillation column enter a second distillation column, wherein the discharge material flow of the bottom of the first distillation column includes the dimethyl carbonate and the second product; and utilizing the second distillation column to separate the dimethyl carbonate in the discharge material flow of the bottom of the first distillation column from the second product.

According to an embodiment of the invention, in the above method for manufacturing the dimethyl carbonate, a methanol feed nozzle may be higher than a carbon dioxide feed nozzle. The carbon dioxide feed nozzle may be higher than a dehydrating agent feed nozzle.

According to an embodiment of the invention, in the above method for manufacturing the dimethyl carbonate, the discharge material flow of the side reactor may enter the first distillation column from a recycle nozzle of the first distillation column. The recycle nozzle may be as high as the dehydrating agent feed nozzle.

According to an embodiment of the invention, in the above method for manufacturing the dimethyl carbonate, the dehydrating agent may be ethylene oxide (EO), and the second product may be ethylene glycol (EG).

According to an embodiment of the invention, in the above method for manufacturing the dimethyl carbonate, splitting a discharge material flow of a top of the first distillation column to form a first split material flow and a second split material flow may further be included. The first split material flow and the second split material flow may include the reactant from the first distillation column.

According to an embodiment of the invention, in the above method for manufacturing the dimethyl carbonate, a flow rate ratio of the first split material flow to the second split material flow may be equal to or less than 30.

According to an embodiment of the invention, in the above method for manufacturing the dimethyl carbonate, a flow rate of the first split material flow may be greater than a flow rate of the second split material flow.

According to an embodiment of the invention, in the above method for manufacturing the dimethyl carbonate, the first split material flow may flow into the side reactor, so as to make the reactant in the first distillation column enter the side reactor.

According to an embodiment of the invention, in the above method for manufacturing the dimethyl carbonate, condensing and flashing the second split material flow to separate out a gas phase material flow including the carbon dioxide and a liquid phase material flow including the methanol may further be included.

According to an embodiment of the invention, in the above method for manufacturing the dimethyl carbonate, the gas phase material flow and the liquid phase material flow may flow back to the first distillation column respectively.

Based on the foregoing description, in the device for manufacturing the dimethyl carbonate proposed by the invention, the methanol supply device and the carbon dioxide supply device are connected to the first distillation column, the feed nozzle of the side reactor is connected to the gas outlet of the top of the first distillation column, and therefore, the reactant including the methanol and the carbon dioxide from the first distillation column may be subjected to the main reaction in the side reactor to form the product including the dimethyl carbonate and the water. In addition, the discharge nozzle of the side reactor is connected to the recycle nozzle of the first distillation column, the dehydrating agent supply device is connected to the first distillation column, and therefore, the product in the side reactor may be made to flow back into the first distillation column, and a dehydrating agent is used to remove the water in the first distillation column. In addition, the dimethyl carbonate may be separated out by the second distillation column. Separating out the product from the first distillation column instantly may drive the main reaction in the side reactor to be conducted continuously, and a product generated by the dehydrating agent and the water may improve relative volatility in the first distillation column. In this way, the device for manufacturing the dimethyl carbonate proposed by the invention can effectively improve the reaction conversion rate and reduce the manufacturing procedure energy consumption, the total annual cost as well as the carbon emission.

In addition, in the method for manufacturing the dimethyl carbonate proposed by the invention, the reactant including the methanol and the carbon dioxide from the first distillation column may be subjected to the main reaction in the side reactor to form the product including the dimethyl carbonate and the water. Then, the discharge material flow of the side reactor is made to flow back to the first distillation column, and the dehydrating agent is used to conduct the dehydrating reaction in the first distillation column, so as to make the dehydrating agent fully react with the water in the first distillation column. Thus, the water in the first distillation column may be completely removed. Therefore, it is not necessary to add additional distillation columns to separate the water, and then a total capital cost (TCC) of equipment can be reduced. Then, the dimethyl carbonate is separated out by the second distillation column. Separating out the product from the first distillation column instantly may drive the main reaction in the side reactor to be conducted continuously, and the product generated by the dehydrating agent and the water may improve the relative volatility in the first distillation column. In this way, the method for manufacturing the dimethyl carbonate proposed by the invention can effectively improve the reaction conversion rate and reduce the manufacturing procedure energy consumption, the total annual cost as well as the carbon emission.

To make the features and advantages of the invention clear and easy to understand, the following gives a detailed description of embodiments with reference to accompanying drawings.

DESCRIPTION OF THE EMBODIMENTS

Figure 1:
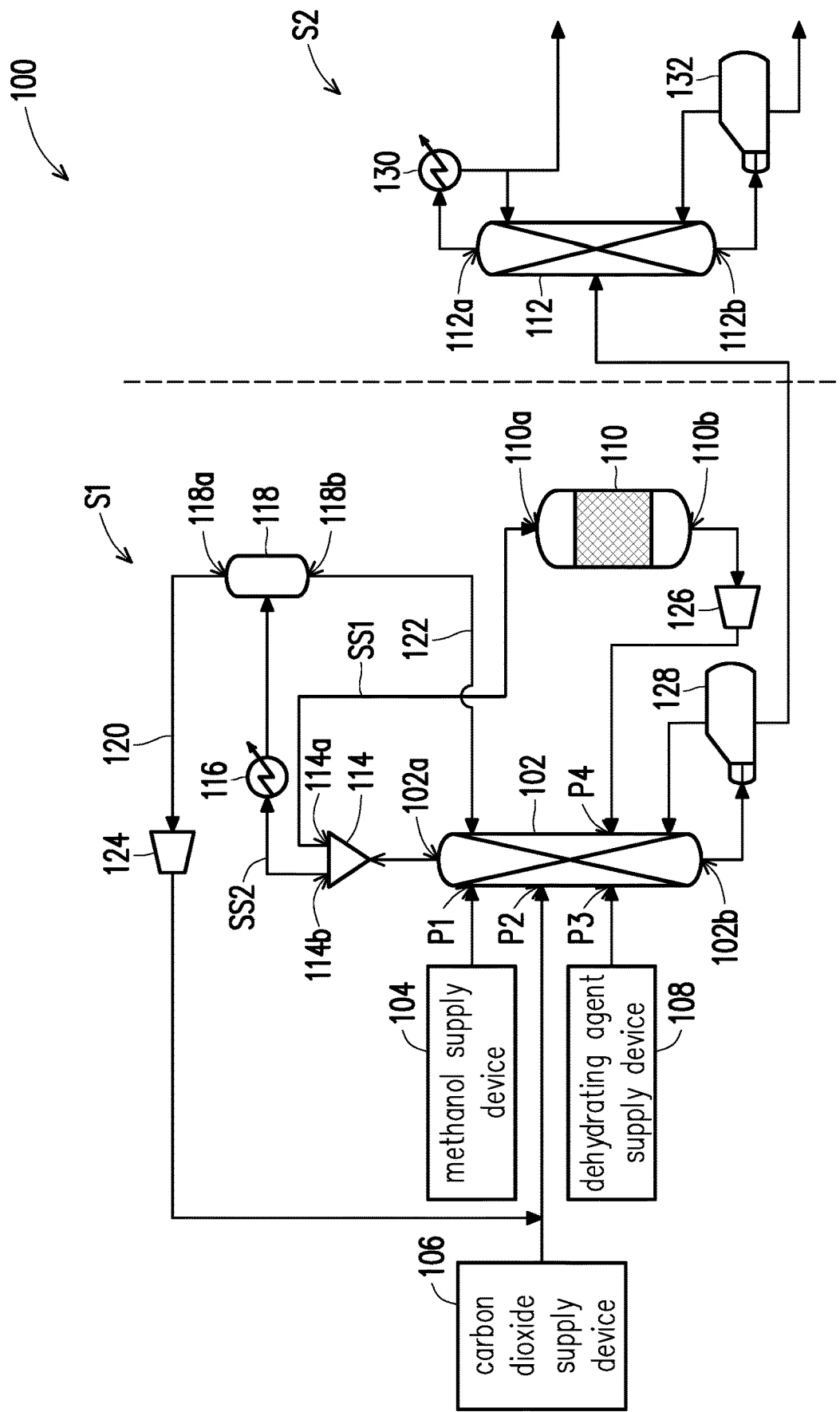
FIG. 1 is a schematic diagram of a device for manufacturing dimethyl carbonate according to an embodiment of the invention.
Figure 2:
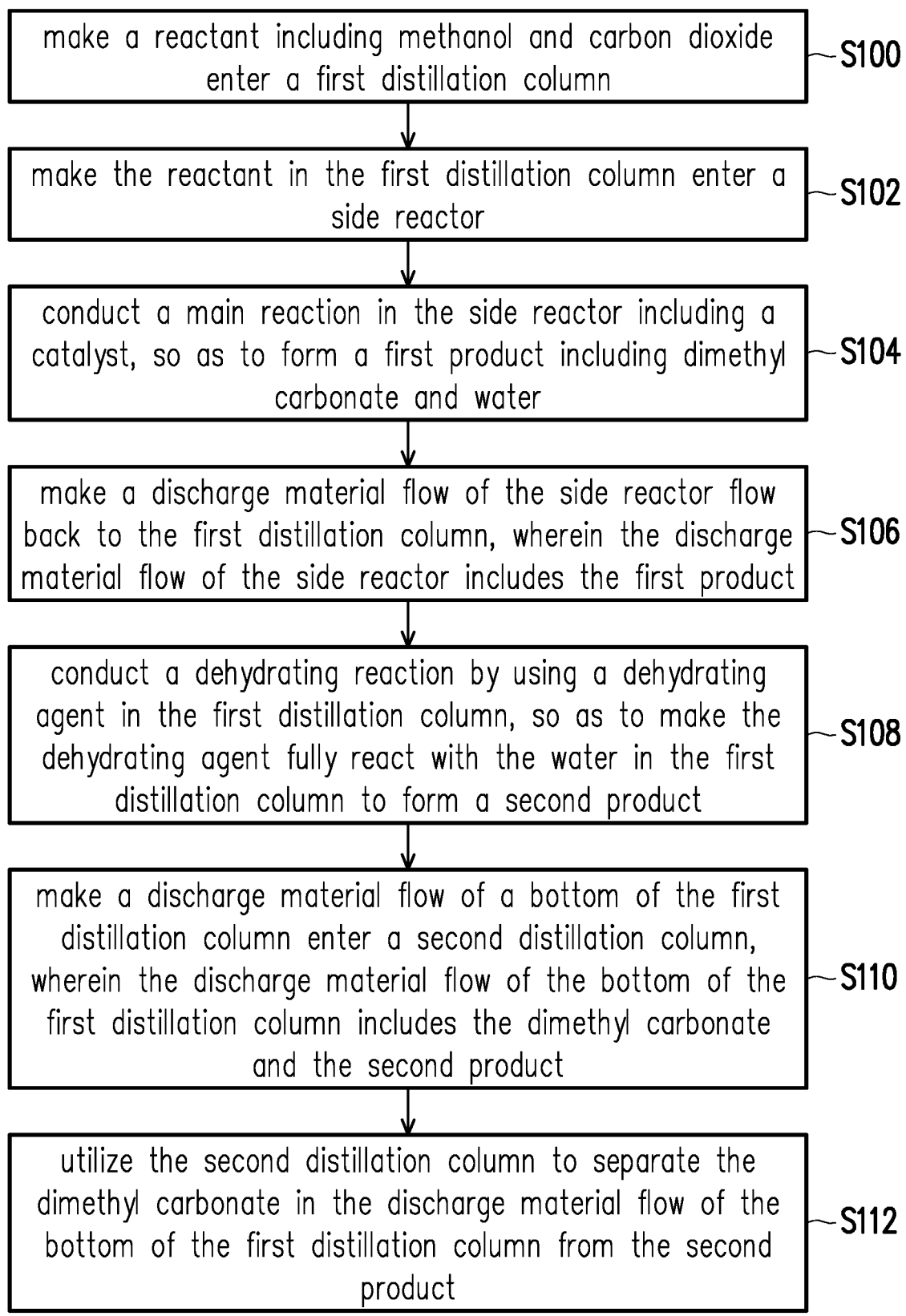
FIG. 2 is a flow diagram of manufacturing dimethyl carbonate according to an embodiment of the invention.

FIG. 1 is a schematic diagram of a device for manufacturing dimethyl carbonate according to an embodiment of the invention. FIG. 2 is a flow diagram of manufacturing dimethyl carbonate according to an embodiment of the invention.

Referring to FIG. 1, which shows a device 100 for manufacturing dimethyl carbonate, the device 100 for manufacturing the dimethyl carbonate includes a reaction section S1 and a separation section S2. The reaction section S1 includes a first distillation column 102, a methanol supply device 104, a carbon dioxide supply device 106, a dehydrating agent supply device 108 and a side reactor 110.

The first distillation column 102 may be provided with a gas outlet 102a of a top and a liquid outlet 102b of a bottom. A discharge material flow of the top of the first distillation column 102 may flow out from the gas outlet 102a of the top. A discharge material flow of the bottom of the first distillation column 102 may flow out from the liquid outlet 102b of the bottom. The first distillation column 102 may be a reactive distillation column.

The methanol supply device 104 is connected to the first distillation column 102, so as to provide methanol into the first distillation column 102. For example, the methanol supply device 104 may be connected to a methanol feed nozzle P1 of the first distillation column 102.

The carbon dioxide supply device 106 is connected to the first distillation column 102, so as to provide carbon dioxide into the first distillation column 102. For example, the carbon dioxide supply device 106 may be connected to a carbon dioxide feed nozzle P2 of the first distillation column 102.

The dehydrating agent supply device 108 is connected to the first distillation column 102, so as to provide a dehydrating agent into the first distillation column 102. For example, the dehydrating agent supply device 108 may be connected to a dehydrating agent feed nozzle P3 of the first distillation column 102. Under the situation that the dehydrating agent is ethylene oxide, the dehydrating agent supply device 108 may be an ethylene oxide supply device, so as to provide the ethylene oxide into the first distillation column 102, but the invention is not limited to this.

In addition, the methanol feed nozzle P1 may be higher than the carbon dioxide feed nozzle P2. The carbon dioxide feed nozzle P2 may be higher than the dehydrating agent feed nozzle P3. For example, under the situation that the first distillation column 102 is a tray distillation column, a column tray corresponding to the methanol feed nozzle P1 may be higher than a column tray corresponding to the carbon dioxide feed nozzle P2, and the column tray corresponding to the carbon dioxide feed nozzle P2 may be higher than a column tray corresponding to the dehydrating agent feed nozzle P3.

A feed nozzle 110a of the side reactor 110 is connected to the gas outlet 102a of the top of the first distillation column 102. A catalyst is disposed in the side reactor 110, that is, the side reactor 110 may be a catalyst reactor. Thus, a reactant including the methanol and the carbon dioxide from the first distillation column 102 may be subjected to a main reaction in the side reactor 110 to form a product including the dimethyl carbonate and water. The product of the main reaction in the side reactor 110 may be a gas phase.

A discharge nozzle 110b of the side reactor 110 is connected to a recycle nozzle P4 of the first distillation column 102. Thus, the product in the side reactor 110 may be made to flow back into the first distillation column 102, and the dehydrating agent is used to conduct a dehydrating reaction in the first distillation column 102. The dehydrating agent in the first distillation column 102 may react with the water to form a product of the dehydrating reaction, so as to remove the water in the first distillation column 102. Under the situation that the dehydrating agent is the ethylene oxide, a product formed by a reaction between the ethylene oxide and the water may be ethylene glycol. The recycle nozzle P4 of the first distillation column 102 may be located between the top and the bottom of the first distillation column 102. The recycle nozzle P4 may be as high as the dehydrating agent feed nozzle P3, which is thus conducive to conducting the dehydrating reaction. For example, under the situation that the first distillation column 102 is the tray distillation column, the recycle nozzle P4 and the dehydrating agent feed nozzle P3 may correspond to the same feed location of column tray in the first distillation column 102.

The separation section S2 includes a second distillation column 112. The second distillation column 112 is connected to the liquid outlet 102b of the bottom of the first distillation column 102, and may be configured to receive the discharge material flow from the bottom of the first distillation column 102, and separate the dimethyl carbonate in the discharge material flow of the bottom from the product (such as the ethylene glycol) of the dehydrating reaction. The second distillation column 112 may be provided with a gas outlet 112a of a top and a liquid outlet 112b of a bottom. A discharge material flow of the top of the second distillation column 112 may flow out from the gas outlet 112a of the top. The discharge material flow of the top of the second distillation column 112 may include the dimethyl carbonate. A discharge material flow of the bottom of the second distillation column 112 may flow out from the liquid outlet 112b of the bottom. The discharge material flow of the bottom of the second distillation column 112 may include the product (such as the ethylene glycol) of the dehydrating reaction.

In addition, under the situation that the above dehydrating reaction may completely remove the water in the first distillation column 102, it is not necessary to add additional distillation columns to separate the water. In this way, the second distillation column 112 may be an only distillation column in the separation section S2, thus the number of distillation columns may be reduced, and then a total capital cost of equipment may be reduced. That is, the second distillation column 112 may be only connected to the first distillation column 102, and not connected to other distillation columns.

In addition, the device 100 for manufacturing the dimethyl carbonate may further include at least one of a splitter 114, a condenser 116, a flash vessel 118, a first backflow pipeline 120, a second backflow pipeline 122, a compressor 124, a compressor 126, a reboiler 128, a condenser 130 and a reboiler 132.

The splitter 114 is connected between the gas outlet 102a of the top of the first distillation column 102 and the feed nozzle 110a of the side reactor 110. The splitter 114 may include a first splitting nozzle 114a and a second splitting nozzle 114b. The first splitting nozzle 114a of the splitter 114 is connected to the feed nozzle 110a of the side reactor 110. The splitter 114 may split the discharge material flow of the top of the first distillation column 102 to form a first split material flow SS1 flowing out from the first splitting nozzle 114a and a second split material flow SS2 flowing out from the second splitting nozzle 114b. The first split material flow SS1 and the second split material flow SS2 may include the reactant from the first distillation column 102. In some embodiments, a flow rate ratio of the first split material flow SS1 to the second split material flow SS2 may be equal to or less than 30. In some embodiments, a flow rate of the first split material flow SS1 may be greater than a flow rate of the second split material flow SS2, and in this way, a better energy saving effect may be realized.

The condenser 116 is connected to the second splitting nozzle 114b of the splitter 114, and may be configured to condense the second split material flow SS2 from the second splitting nozzle 114b. The flash vessel 118 is connected to the condenser 116. The flash vessel 118 may be provided with a gas outlet 118a and a liquid outlet 118b. A gas phase material flow of the flash vessel 118 may flow out from the gas outlet 118a of the flash vessel 118. The gas phase material flow of the flash vessel 118 may include the carbon dioxide. A liquid phase material flow of the flash vessel 118 may flow out from the liquid outlet 118b of the flash vessel 118. The liquid phase material flow of the flash vessel 118 may include the methanol.

The first backflow pipeline 120 is connected between the gas outlet 118a of the flash vessel 118 and the first distillation column 102, so as to make the gas phase material flow of the flash vessel 118 flow back to the first distillation column 102. The first backflow pipeline 120 may be connected to the carbon dioxide feed nozzle P2 of the first distillation column 102. The second backflow pipeline 122 is connected between the liquid outlet 118b of the flash vessel 118 and the first distillation column 102, so as to make the liquid phase material flow of the flash vessel 118 flow back to the first distillation column 102.

The compressor 124 is located on the first backflow pipeline 120 between the gas outlet 118a of the flash vessel 118 and the first distillation column 102, which is thus conducive to making the gas phase material flow of the flash vessel 118 flow back to the first distillation column 102.

The compressor 126 is located between the discharge nozzle 110b of the side reactor 110 and the recycle nozzle P4 of the first distillation column 102, which is thus conducive to making the product in the side reactor 110 flow back into the first distillation column 102.

The reboiler 128 is connected to the first distillation column 102, so as to heat the first distillation column 102. The condenser 130 is connected to the gas outlet 112a of the top of the second distillation column 112, so as to cool the discharge material flow of the top of the second distillation column 112. The reboiler 132 is connected to the second distillation column 112, so as to heat the second distillation column 112.

Based on the above embodiment, it can be known that in the device 100 for manufacturing the dimethyl carbonate, the methanol supply device 104 and the carbon dioxide supply device 106 are connected to the first distillation column 102, the feed nozzle 110a of the side reactor 110 is connected to the gas outlet 102a of the top of the first distillation column 102, and therefore, the reactant including the methanol and the carbon dioxide from the first distillation column 102 may be subjected to the main reaction in the side reactor 110 to form the product including the dimethyl carbonate and the water. In addition, the discharge nozzle 110b of the side reactor 110 is connected to the recycle nozzle P4 of the first distillation column 102, the dehydrating agent supply device 108 is connected to the first distillation column 102, therefore, the product in the side reactor 110 may be made to flow back into the first distillation column 102, and the dehydrating agent is used to remove the water in the first distillation column 102. In addition, the dimethyl carbonate may be separated out by the second distillation column 112. Separating out the product from the first distillation column 102 instantly may drive the main reaction in the side reactor 110 to be conducted continuously, and the product generated by the dehydrating agent and the water may improve relative volatility in the first distillation column 102. In this way, the device 100 for manufacturing the dimethyl carbonate can effectively improve a reaction conversion rate and reduce manufacturing procedure energy consumption, a total annual cost as well as carbon emission.

A method for manufacturing dimethyl carbonate is illustrated by FIG. 1 and FIG. 2 below.

Referring to FIG. 1 and FIG. 2, step S100 is conducted to make a reactant including methanol and carbon dioxide enter a first distillation column 102. For example, the methanol and the carbon dioxide may be provided into the first distillation column 102 by a methanol supply device 104 and a carbon dioxide supply device 106 respectively.

Step S102 is conducted to make the reactant in the first distillation column 102 enter a side reactor 110. In some embodiments, a discharge material flow of a top of the first distillation column 102 may be split to form a first split material flow SS1 and a second split material flow SS2. The first split material flow SS1 and the second split material flow SS2 may include the reactant from the first distillation column 102. For example, the discharge material flow of the top of the first distillation column 102 may be split by the splitter 114 to form the first split material flow SS1 flowing out from a first splitting nozzle 114a and the second split material flow SS2 flowing out from a second splitting nozzle 114b. The first split material flow SS1 may flow into the side reactor 110, so as to make the reactant in the first distillation column 102 enter the side reactor 110. In some embodiments, a flow rate ratio of the first split material flow SS1 to the second split material flow SS2 may be equal to or less than 30. In some embodiments, a flow rate of the first split material flow SS1 may be greater than a flow rate of the second split material flow SS2, and in this way, a better energy saving effect may be realized.

In addition, the second split material flow SS2 may be condensed and flashed to separate out a gas phase material flow including the carbon dioxide and a liquid phase material flow including the methanol. The gas phase material flow and the liquid phase material flow may flow back to the first distillation column 102 respectively. For example, the second split material flow SS2 may be condensed and flashed by a condenser 116 and a flash vessel 118. The gas phase material flow of the flash vessel 118 may flow back to the first distillation column 102 by a first backflow pipeline 120 and a compressor 124. In some embodiments, the gas phase material flow of the flash vessel 118 may enter the first distillation column 102 from a carbon dioxide feed nozzle P2 of the first distillation column 102. The liquid phase material flow of the flash vessel 118 may flow back to the first distillation column 102 by a second backflow pipeline 122.

Step S104 is conducted, and a main reaction is conducted in the side reactor 110 including a catalyst, so as to form a first product including the dimethyl carbonate (DMC) and water. The catalyst, for example, is a copper/nickel/graphite nanocomposite.

A reaction path of the main reaction is as shown in the following formula 1:

$$CO_2 + 2MeOH \rightarrow DMC + H_2O \qquad \text{formula 1}$$

Step S106 is conducted to make a discharge material flow of the side reactor 110 flow back to the first distillation column 102. The discharge material flow of the side reactor 110 includes the first product. For example, the discharge material flow of the side reactor 110 may be made to flow back to the first distillation column 102 by the compressor 124. The discharge material flow of the side reactor 110 may enter the first distillation column 102 from a recycle nozzle P4 of the first distillation column. The recycle nozzle P4 may be as high as a dehydrating agent feed nozzle P3, which is thus conducive to conducting a subsequent dehydrating reaction. In addition, under the situation that the method for manufacturing the dimethyl carbonate is in a continuous manufacturing procedure, the discharge material flow of the side reactor 110 may further include an unreacted reactant besides the first product.

Step S108 is conducted, and a dehydrating agent is used to conduct the dehydrating reaction in the first distillation column 102, so as to make the dehydrating agent fully react with water in the first distillation column 102 to form a second product. For example, the dehydrating agent may be provided into the first distillation column 102 by a dehydrating agent supply device 108. The dehydrating agent may be ethylene oxide (EO), and the second product may be ethylene glycol (EG).

Under the situation that the dehydrating agent is the EO, a reaction path of the dehydrating reaction is as shown in the following formula 2:

$$EO + H_2O \rightarrow EG \qquad \text{formula 2}$$

Step S110 is conducted to make a discharge material flow of a bottom of the first distillation column 102 enter a second distillation column 112. The discharge material flow of the bottom of the first distillation column 102 includes the dimethyl carbonate and the second product.

Step S112 is conducted, and the second distillation column 112 is utilized to separate the dimethyl carbonate in the discharge material flow of the bottom of the first distillation column 102 from the second product. For example, a discharge material flow of a top of the second distillation column 112 may include the dimethyl carbonate, and the discharge material flow of the top of the second distillation column 112 may be cooled by a condenser 130. A discharge material flow of a bottom of the second distillation column 112 may include a second product (such as the ethylene glycol) of the dehydrating reaction.

Based on the above embodiment, it can be known that in the above method for manufacturing the dimethyl carbonate, the reactant including the methanol and the carbon dioxide from the first distillation column 102 may be subjected to the main reaction in the side reactor 110 to form the product including the dimethyl carbonate and the water. Then, the discharge material flow of the side reactor 110 is made to flow back to the first distillation column 102, and the dehydrating agent is used to conduct the dehydrating reaction in the first distillation column 102, so as to make the dehydrating agent fully react with the water in the first distillation column 102. Thus, the water in the first distillation column 102 may be completely removed. Therefore, it is not necessary to add additional distillation columns to separate the water, and then a total capital cost of equipment may be reduced. Then, the dimethyl carbonate is separated out by the second distillation column 112. Separating out the product from the first distillation column 102 instantly may drive the main reaction in the side reactor 110 to be conducted continuously, and the product generated by the dehydrating agent and the water may improve relative volatility in the first distillation column 102. In this way, the above method for manufacturing the dimethyl carbonate can effectively improve a reaction conversion rate and reduce manufacturing procedure energy consumption, a total annual cost as well as carbon emission.

Based on the foregoing, in the device and method for manufacturing the dimethyl carbonate proposed by the above embodiments, the reactant from the first distillation column may be subjected to the main reaction in the side reactor, the discharge material flow of the side reactor flows back into the first distillation column to be subjected to the dehydrating reaction by using the dehydrating agent, and the dimethyl carbonate may be separated out by the second distillation column. Thus, the reaction conversion rate can be effectively improved, and the manufacturing procedure energy consumption, the total annual cost as well as the carbon emission can be effectively reduced.

Although the invention is described with reference to the above embodiments, the embodiments are not intended to limit the invention. A person of ordinary skill in the art may make variations and modifications without departing from the spirit and scope of the invention. Therefore, the protection scope of the invention should be subject to the appended claims.

What is claimed is:

1. A device for manufacturing dimethyl carbonate, comprising:
    a reaction section comprising:
        a first distillation column;
        a methanol supply device connected to the first distillation column;
        a carbon dioxide supply device connected to the first distillation column;
        a dehydrating agent supply device connected to the first distillation column; and
        a side reactor, wherein a feed nozzle of the side reactor is connected to a gas outlet of a top of the first distillation column, a discharge nozzle of the side reactor is connected to a recycle nozzle of the first distillation column, and a catalyst is disposed in the side reactor; and
    a separation section comprising:
        a second distillation column connected to a liquid outlet of a bottom of the first distillation column.

2. The device for manufacturing the dimethyl carbonate according to claim 1, wherein the second distillation column is an only distillation column in the separation section.

3. The device for manufacturing the dimethyl carbonate according to claim 1, wherein the second distillation column is only connected to the first distillation column and is not connected to other distillation columns.

4. The device for manufacturing the dimethyl carbonate according to claim 1, wherein the recycle nozzle of the first distillation column is located between the top and the bottom of the first distillation column.

5. The device for manufacturing the dimethyl carbonate according to claim 1, wherein
    the methanol supply device is connected to a methanol feed nozzle of the first distillation column,
    the carbon dioxide supply device is connected to a carbon dioxide feed nozzle of the first distillation column, and
    the dehydrating agent supply device is connected to a dehydrating agent feed nozzle of the first distillation column.

6. The device for manufacturing the dimethyl carbonate according to claim 5, wherein the methanol feed nozzle is higher than the carbon dioxide feed nozzle, and the carbon dioxide feed nozzle is higher than the dehydrating agent feed nozzle.

7. The device for manufacturing the dimethyl carbonate according to claim 5, wherein the recycle nozzle is as high as the dehydrating agent feed nozzle.

8. The device for manufacturing the dimethyl carbonate according to claim 1, further comprising:
    a splitter connected between the gas outlet of the top of the first distillation column and the feed nozzle of the side reactor, and comprising a first splitting nozzle and a second splitting nozzle, wherein the first splitting nozzle of the splitter is connected to the feed nozzle of the side reactor.

9. The device for manufacturing the dimethyl carbonate according to claim 8, further comprising:

a condenser connected to the second splitting nozzle of the splitter; and a flash vessel connected to the condenser.

10. The device for manufacturing the dimethyl carbonate according to claim 9, further comprising:

a first backflow pipeline connected between a gas outlet of the flash vessel and the first distillation column; and a second backflow pipeline connected between a liquid outlet of the flash vessel and the first distillation column.

11. A method for manufacturing dimethyl carbonate, comprising:

making a reactant comprising methanol and carbon dioxide enter a first distillation column, wherein the methanol is provided into the first distillation column by a methanol supply device, the carbon dioxide is provided into the first distillation column by a carbon dioxide supply device, the methanol supply device is connected to the first distillation column, and the carbon dioxide supply device is connected to the first distillation column;

making the reactant in the first distillation column enter a side reactor, wherein a feed nozzle of the side reactor is connected to a gas outlet of a top of the first distillation column, a discharge nozzle of the side reactor is connected to a recycle nozzle of the first distillation column, and a catalyst is disposed in the side reactor;

conducting a main reaction in the side reactor comprising the catalyst, so as to form a first product comprising the dimethyl carbonate and water;

making a discharge material flow of the side reactor flow back to the first distillation column, wherein the discharge material flow of the side reactor comprises the first product;

conducting a dehydrating reaction in the first distillation column by using a dehydrating agent, so as to make the dehydrating agent fully react with the water in the first distillation column to form a second product, wherein the dehydrating agent is provided into the first distillation column by a dehydrating agent supply device, and the dehydrating agent supply device is connected to the first distillation column;

making a discharge material flow of a bottom of the first distillation column enter a second distillation column, wherein the discharge material flow of the bottom of the first distillation column comprises the dimethyl carbonate and the second product, and the second distillation column is connected to a liquid outlet of the bottom of the first distillation column; and utilizing the second distillation column to separate the dimethyl carbonate in the discharge material flow of the bottom of the first distillation column from the second product.

12. The method for manufacturing the dimethyl carbonate according to claim 11, wherein a methanol feed nozzle is higher than a carbon dioxide feed nozzle, and the carbon dioxide feed nozzle is higher than a dehydrating agent feed nozzle.

13. The method for manufacturing the dimethyl carbonate according to claim 11, wherein the discharge material flow of the side reactor enters the first distillation column from the recycle nozzle of the first distillation column, and the recycle nozzle is as high as a dehydrating agent feed nozzle.

14. The method for manufacturing the dimethyl carbonate according to claim 11, wherein the dehydrating agent comprises ethylene oxide, and the second product comprises ethylene glycol.

15. The method for manufacturing the dimethyl carbonate according to claim 11, further comprising:

splitting a discharge material flow of the top of the first distillation column to form a first split material flow and a second split material flow, wherein the first split material flow and the second split material flow comprise the reactant from the first distillation column.

16. The method for manufacturing the dimethyl carbonate according to claim 15, wherein a flow rate ratio of the first split material flow to the second split material flow is equal to or less than 30.

17. The method for manufacturing the dimethyl carbonate according to claim 15, wherein a flow rate of the first split material flow is greater than a flow rate of the second split material flow.

18. The method for manufacturing the dimethyl carbonate according to claim 15, wherein the first split material flow enters the side reactor, so as to make the reactant in the first distillation column enter the side reactor.

19. The method for manufacturing the dimethyl carbonate according to claim 15, further comprising:

condensing and flashing the second split material flow to separate out a gas phase material flow comprising the carbon dioxide and a liquid phase material flow comprising the methanol.

20. The method for manufacturing the dimethyl carbonate according to claim 19, wherein the gas phase material flow and the liquid phase material flow back to the first distillation column respectively.

* * * * *